US00PP33558P2

(12) United States Plant Patent
Hartman

(10) Patent No.: US PP33,558 P2
(45) Date of Patent: Oct. 12, 2021

(54) ***CALADIUM* PLANT NAMED 'GPR 013-2243'**

(50) Latin Name: ***Caladium* X *hortulanum***
Varietal Denomination: GPR 013-2243

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/013,767

(22) Filed: Sep. 7, 2020

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. Anne Whealy

(57) ABSTRACT

A new and distinct cultivar of *Caladium* plant named 'GPR 013-2243', characterized by its intermediate height; somewhat mounding plant habit; dense and bushy appearance; vigorous growth habit; rapid growth rate; thick and rigid lance-type leaves that are white to light greyed green in color variably flushed and tinged with purplish pink to red and with dark green-colored margins and venation; petioles that are black or black with tannish pink stripes in color; and excellent garden performance with tolerance to full sunlight, wind and rain.

6 Drawing Sheets

Figure 1:
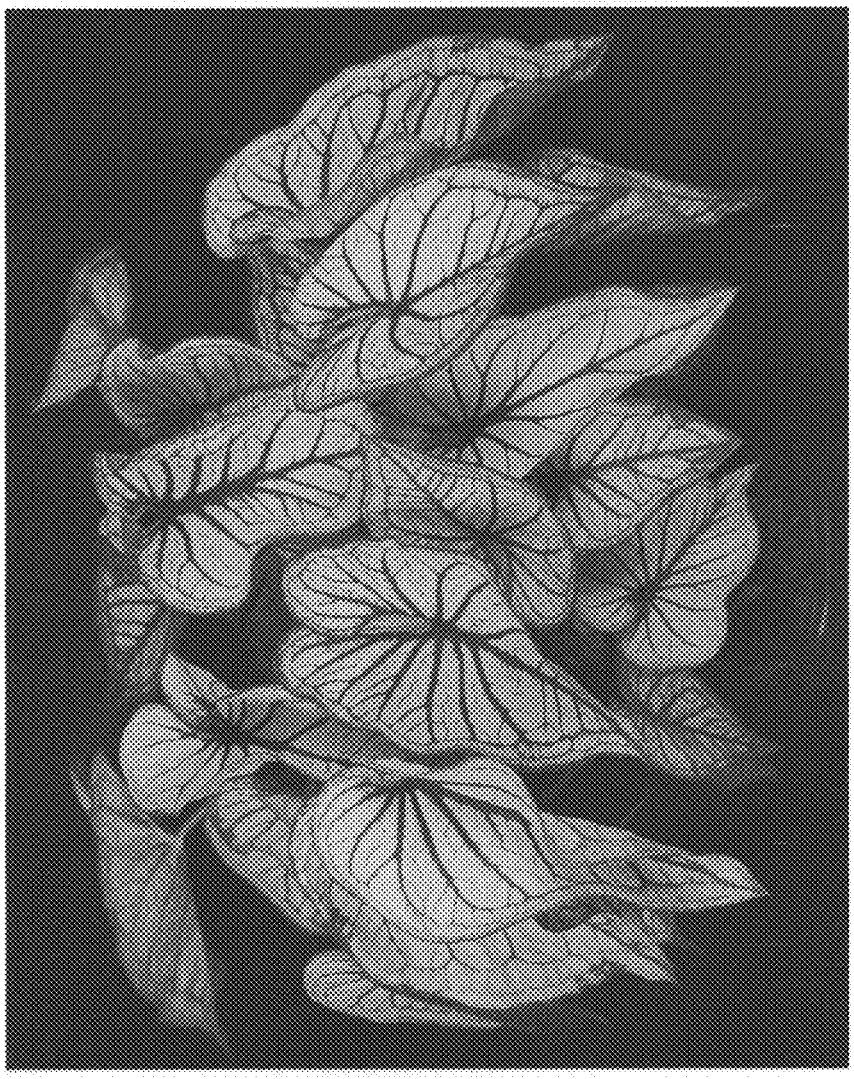

Botanical designation: *Caladium* X *hortulanum*.
Cultivar denomination: 'GPR 013-2243'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'GPR 013-2243'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'White Wonder', disclosed in U.S. Plant Pat. No. 21,044, as the female, or seed, parent with *Caladium* X *hortulanum* 'Green Pearl', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'GPR 013-2243'. These characteristics in combination distinguish 'GPR 013-2243' as a new and distinct *Caladium* plant:

1. Intermediate in height and somewhat mounding plant habit; dense and bushy appearance.
2. Vigorous growth habit and rapid growth rate.
3. Thick and rigid lance-type leaves that are white to light greyed green in color variably flushed and tinged with purplish pink to red and with dark green-colored margins and venation.
4. Petioles that are black or black with tannish pink stripes in color.
5. Excellent garden performance with tolerance to full sunlight, wind and rain.

Plants of the new *Caladium* differ primarily from plants of the female parent, 'White Wonder', in the following characteristics:

1. Leaves of plants of the new *Caladium* are thicker than leaves of plants of 'White Wonder'.

2. Plants of the new *Caladium* and 'White Wonder' differ in leaf color as leaves of the new *Caladium* are white to light greyed green in color variably flushed and tinged with purplish pink to red with dark green-colored margins and venation whereas leaves of 'White Wonder' are white to grey-green in color with light pink to white-colored venation and dark green-colored borders.
3. Plants of the new *Caladium* and 'White Wonder' differ in leaf petiole color as leaf petioles of the new *Caladium* are black or black with tannish pink stripes in color whereas leaf petioles of 'White Wonder' are tannish green with black stripes in color.

Plants of the new *Caladium* differ primarily from plants of the male parent, 'Green Pearl', in the following characteristics:

1. Plants of the new *Caladium* grow faster than plants of 'Green Pearl'.
2. Leaves of plants of the new *Caladium* are thicker than leaves of plants of 'Green Pearl'.
3. Plants of the new *Caladium* and 'Green Pearl' differ in leaf color as leaves of the new *Caladium* are white to light greyed green in color variably flushed and tinged with purplish pink to red with dark green-colored margins and venation whereas leaves of 'Green Pearl' are predominately white or greenish white in color with green to dark green-colored venation and green-colored margins.
4. Plants of the new *Caladium* and 'Green Pearl' differ in leaf petiole color as leaf petioles of the new *Caladium* are black or black with tannish pink stripes in color whereas leaf petioles of 'Green Pearl' are green to tannish green in color.

Plants of the new *Caladium* can be compared to plants of *Caladium* X *hortulanum* 'Florida Sweetheart', disclosed in U.S. Plant Pat. No. 8,526. In side-by-side comparisons, plants of the new *Caladium* differ primarily from plants of 'Florida Sweetheart' in the following characteristics:

1. Plants of the new *Caladium* are taller than plants of 'Florida Sweetheart'.
2. Leaves of plants of the new *Caladium* are thicker than leaves of plants of 'Florida Sweetheart'.
3. Plants of the new *Caladium* and 'Florida Sweetheart' differ in leaf color as leaves of the new *Caladium* are white to light greyed green in color variably flushed and tinged with purplish pink to red with dark green-colored margins and venation whereas leaves of 'Florida Sweetheart' have dark pink-colored venation, rose pink-colored interveinal areas with greenish white-colored margins.
4. Plants of the new *Caladium* and 'Florida Sweetheart' differ in leaf petiole color as leaf petioles of the new *Caladium* are black or black with tannish pink stripes in color whereas leaf petioles of 'Florida Sweetheart' are tannish pink with dark stripes in color.

Plants of the new *Caladium* can also be compared to plants of *Caladium* X *hortulanum* 'Xplosion', disclosed in U.S. Plant Pat. No. 31,570. In side-by-side comparisons, plants of the new *Caladium* differ primarily from plants of 'Xplosion' in the following characteristics:

1. Plants of the new *Caladium* and 'Xplosion' differ in leaf color as leaves of the new *Caladium* are white to light greyed green in color variably flushed and tinged with purplish pink to red with dark green-colored margins and venation whereas leaves of 'Xplosion' are dark green tinged with greyed purple in color with red purple to dark red-colored venation and interveinal areas that are white in color with light red-colored spots.
2. Plants of the new *Caladium* and 'Xplosion' differ in leaf petiole color as leaf petioles of the new *Caladium* are black or black with tannish pink stripes in color whereas leaf petioles of 'Xplosion' are tannish pink to tannish green with darker brown-colored stippling and streaks.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'GPR 013-2243' in a container and grown in a shade house (tuber de-eyed).

Figure 2:
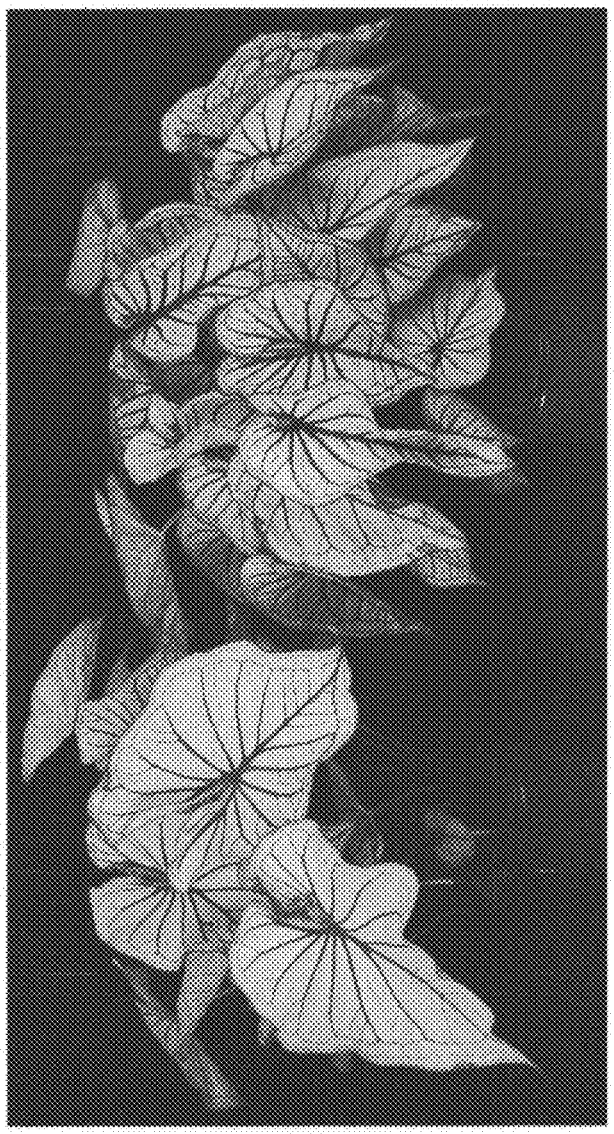
Figure 3:
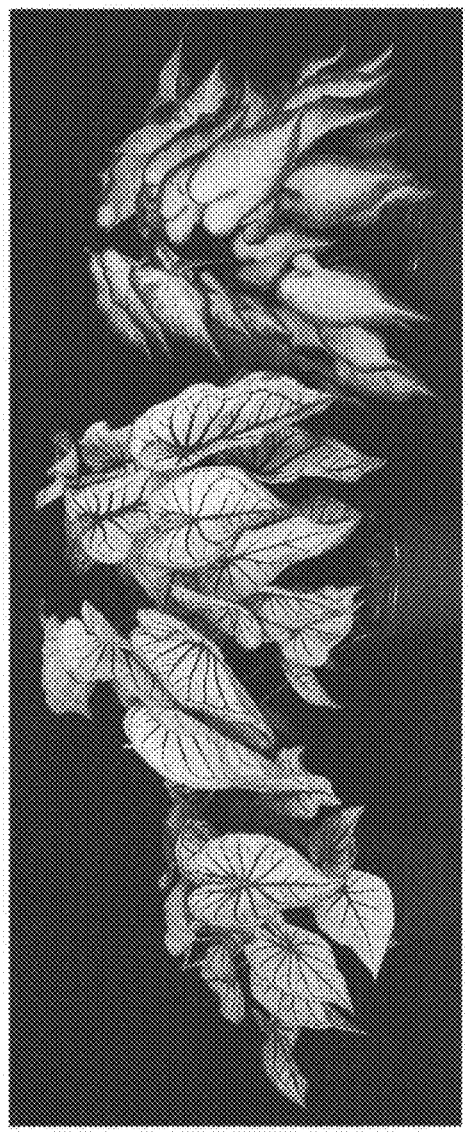

The photograph on the second sheet (FIG. 2) is a comparison view of typical plants of 'GPR 013-2243' grown in containers, the plant on the left has not had its tuber de-eyed and the plant on the right has had its tuber de-eyed prior to planting;

the photograph on the third sheet (FIG. 3) is side perspective view of the male parent, 'Green Pearl' (left), 'GPR 013-2243' (center) and the female parent, 'White Wonder' (right).

Figure 4:
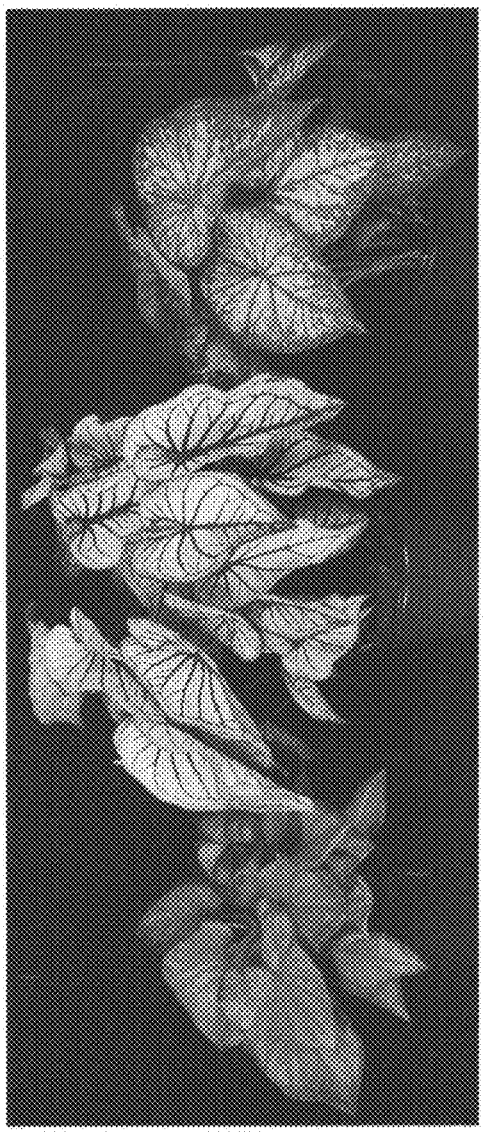

The photograph on the fourth sheet (FIG. 4) is a comparison view of typical potted plants of 'Florida Sweetheart' (left), 'GPR 013-2243' (center) and 'Xplosion' (right).

Figure 5:
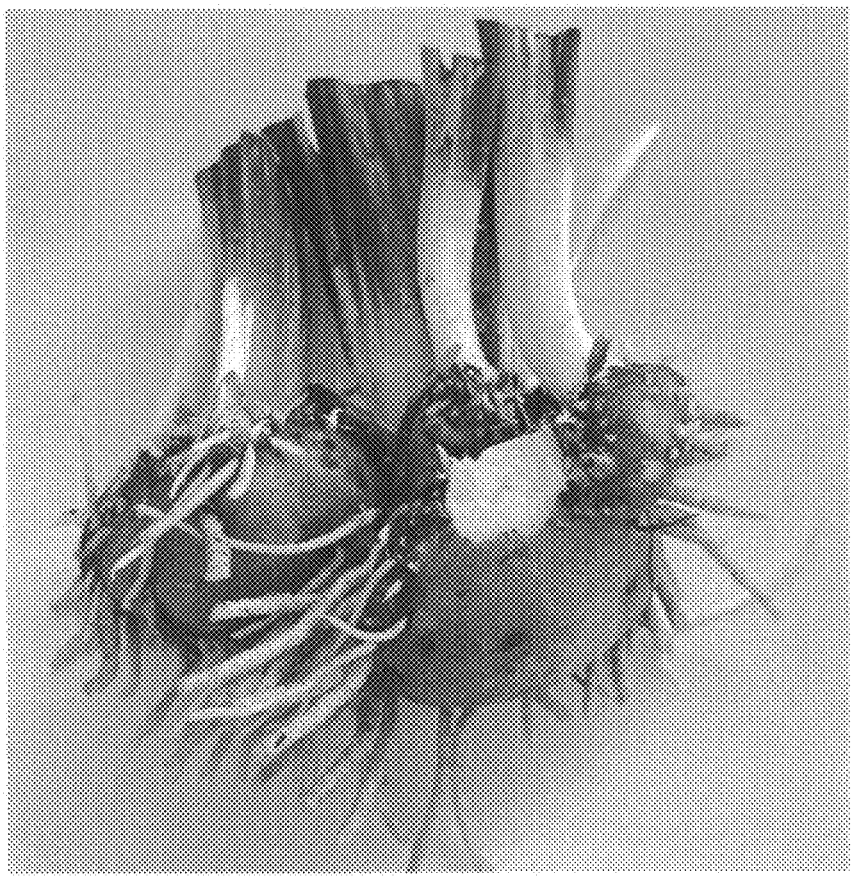

The photograph on the fifth sheet (FIG. 5) is a close-up view of typical freshly-harvested tubers with roots and leaf petioles of 'GPR 013-2243'.

Figure 6:
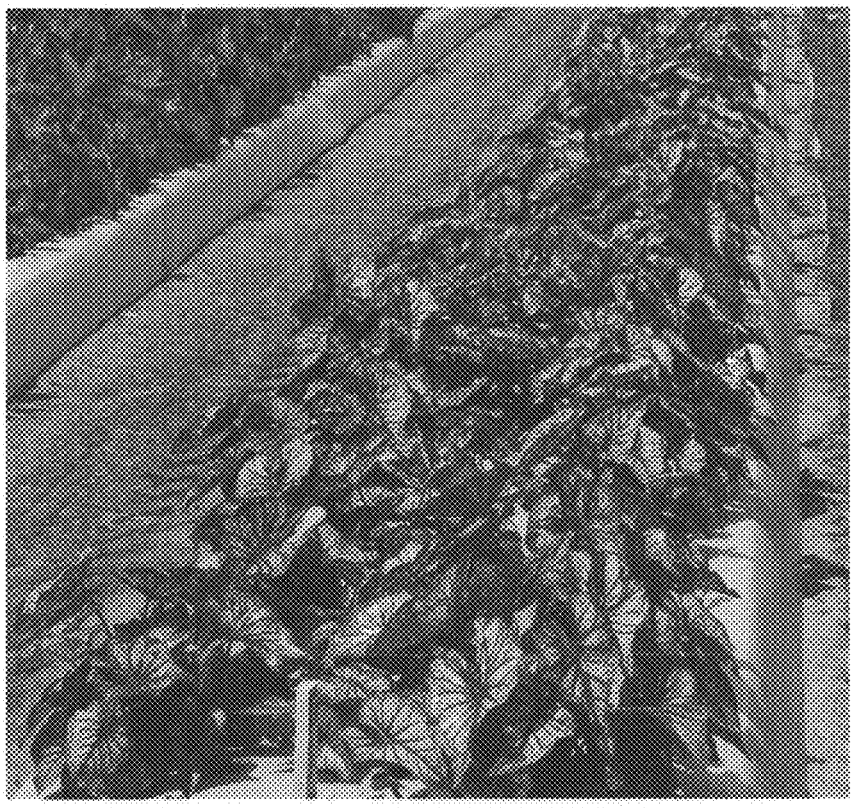

The photograph on the sixth sheet (FIG. 6) is a side perspective view of typical plants of 'GPR 013-2243' grown in an open production field.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were eight weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'GPR 013-2243'.

Parentage:

*Female, or seed, parent.*—*Caladium* X *hortulanum* 'White Wonder', disclosed in U.S. Plant Pat. No. 21,044.

*Male, or pollen, parent.*—*Caladium* X *hortulanum* 'Green Pearl', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments ovate to elliptic in shape. Height: About 3 cm to 3.9 cm. Diameter: About 7.8 cm to 9.8 cm. Segment height: About 2 cm to 2.5 cm. Segment diameter: About 1.6 cm to 1.7 cm. Axillary bud shape: Roughly triangular. Axillary bud size: About 6 mm by 11 mm. Texture: Thick, starchy; somewhat brittle. Color: Periderm, fleshly-harvested: Close to 199B. Periderm, dried: Close to 200A to 200B. Epidermis: Initially, close to 159B becoming closer to 155B with development. Cortical tissue: Close to 10C and 10D. Axillary buds: Close to 49C. Root description: Thick, fleshy contractile roots with few lateral branches; color, close to NN155D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Intermediate in height, upright and somewhat mounding plant habit; dense and bushy appearance; vigorous growth habit and rapid growth rate; potted plants finish in saleable form in about four to six weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 39 cm to 41.5 cm.

*Plant height, from soil level to top of foliar plane, shade house-grown potted plants, tubers not de-eyed*.—About 38 cm to 43 cm.

*Plant diameter or spread, shade house-grown potted plants, tubers de-eyed*.—About 47 cm to 53 cm.

*Plant diameter or spread, shade house-grown potted plants, tubers not de-eyed*.—About 43 cm to 52 cm.

*Number of shoots per plant, shade house-grown potted plants, tubers de-eyed*.—About four to seven develop per #1 tuber.

*Number of shoots per plant, shade house-grown potted plants, tubers not de-eyed*.—About three to four develop per #1 tuber.

*Cataphylls, shade house-grown potted plants*.—Length: About 4 cm to 7.6 cm. Width: About 1.6 cm to 1.9 cm. Shape: Linear to narrowly elliptic. Apex: Acute, emarginate. Base: Sheathing the stem. Color: Outer surface: Close to N155B to N155C with stippling, streaks and marbling, close to N200A tinged with close to 202A; color becoming closer to 200A with development. Inner surface: Close to N155B; colors and patterns on outer surface visible on inner surface.

Leaf description:

*Arrangement and type*.—Alternate; simple; lance-type.

*Length, shade house-grown potted plants*.—About 16 cm to 26 cm.

*Width, shade house-grown potted plants*.—About 10.5 cm to 16.5 cm; when flattened, about 18 cm.

*Shape*.—Ovate.

*Apex*.—Acute to acuminate.

*Base*.—Sagittate-peltate, cordate; basal leaf lobes may be imbricate.

*Margin*.—Entire; wavy with broad undulations.

*Texture and luster, upper surface*.—Smooth, glabrous; relatively thick; slightly rugose between veins; slightly carinate; dull sheen.

*Texture and luster, lower surface*.—Smooth, glabrous; at the center and surrounding veins, glaucous; dull sheen.

*Venation pattern*.—Pinnate and palmate.

*Color, shade house-grown potted plants*.—Fully developed leaves, upper surface: Background color: Close to NN155C, NN155B, 190C variably flushed and tinged with close to 51C, 58D, 181B, 181C and 182D. Margins: Close to N189A at the leaf edge, close to 183A. Basal notch: Close to 187A. Midvein and primary venation: Close to N189A and NN137A variably flushed with close to N186C, 202A, 53A and 46A. Secondary venation: Close to N189A and 139A. Fully developed leaves, lower surface: Background color: Close to 157D, 1470, 137C and 145D faintly and variably flushed with close to 200C, 178A, 187A and 181D. Margins: Close to 191A and 189A at the leaf edge, close to 187A and 187B. Leaf attachment point: Close to 187A and 187B. Midvein: Close to 195B, 195C, 199D and 148B; areas surrounding midvein, close to 137C variably flushed, streaked and marked with close to 200A and 183A. Primary venation: Close to 145B, 145C and 148B; areas surrounding primary venation, close to 137C variably flushed and marked with close to 200A and 183A. Secondary venation: Close to 189A, 147C, 157A, 157B and 145D.

*Petioles*.—Aspect: Initially upright and straight and leaning outwardly with development; occasionally, arched and curved outwardly; flexible. Length, shade house-grown potted plants: About 16 cm to 36 cm. Diameter, distally, shade house-grown potted plants: About 4.8 mm to 7 mm. Diameter, proximally, shade house-grown potted plants: About 7 mm to 9 mm. Texture and luster: Smooth, glabrous; glaucous. Color, shade house-grown potted plants: When developing and fully developed: Close to 202A tinged with close to N200A or close to N200A tinged with 202A and streaked and striped with close to N170D; just below the leaf junction, close to N200A tinged with close to 202A and striped with close to N155B tinged with close to 65D. Wing length, shade house-grown potted plants: About 6.2 cm to 8.5 cm. Wing diameter, shade house-grown potted plants: About 8 mm to 11 mm. Texture and luster, inner and outer surfaces: Smooth, glabrous; dull to slightly glossy. Wing color, shade house-grown potted plants: Outer surface: Close to N155B and N155C with stippling, streaks and marbling of close to N200A tinged with close to 202A. Inner surface: Close to N155B; colors and patterns on the outer surface are visible on the inner surface.

Inflorescence description: To date, inflorescence development has not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Garden performance & temperature tolerance: Plants of the new *Caladium* have been observed to have excellent garden performance with tolerance to full sunlight, wind and rain and to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'GPR 013-2243' as illustrated and described.

* * * * *